(12) United States Patent
De Klerk et al.

(10) Patent No.: US 10,906,680 B2
(45) Date of Patent: Feb. 2, 2021

(54) STERILISATION BAG (75) Inventors: Christo Andre De Klerk, Queensland (AU); Terry Dean Kemp, Auckland (NZ)

(73) Assignee: MERCER TECHNOLOGIES LIMITED, Auckland (NZ)

(*) Notice: Subject to any disclaimer, the term of this patent is extended or adjusted under 35 U.S.C. 154(b) by 260 days.

(21) Appl. No.: 13/201,168

(22) PCT Filed: Feb. 12, 2010

(86) PCT No.: PCT/NZ2010/000021
§ 371 (c)(1),
(2), (4) Date: Nov. 15, 2011

(87) PCT Pub. No.: WO2010/093265
PCT Pub. Date: Aug. 19, 2010

(65) Prior Publication Data
US 2012/0057810 A1 Mar. 8, 2012

(30) Foreign Application Priority Data

Feb. 13, 2009 (NZ) .................................. 574909
Feb. 13, 2009 (NZ) .................................. 574912

(51) Int. Cl.
*B65D 33/00* (2006.01)
*B65B 55/18* (2006.01)
*A61L 2/26* (2006.01)

(52) U.S. Cl.
CPC ............... *B65B 55/18* (2013.01); *A61L 2/26* (2013.01); *A61L 2202/181* (2013.01)

(58) Field of Classification Search
CPC .. B65D 88/1668; B65D 77/225; B65D 33/01; B65B 55/18; A61L 2/26; A61L 2202/181
(Continued)

(56) References Cited

U.S. PATENT DOCUMENTS 4,057,144 A   11/1977 Schuster
4,644,586 A * 2/1987 Padgett ..................... 383/102
(Continued)

FOREIGN PATENT DOCUMENTS

EP    846445    6/1998
EP    1683469   7/2006
(Continued)

OTHER PUBLICATIONS

Mercer Technologies Limited, International Search Report and Written Opinion dated Aug. 5, 2010, PCT Appln. No. PCT/NZ2010/000021 filed Feb. 12, 2010 (9 pages).
(Continued)

*Primary Examiner* — Jes F Pascua
*Assistant Examiner* — Nina K Attel
(74) *Attorney, Agent, or Firm* — Thomas Coester Intellectual Property Law Corporation (57) ABSTRACT

The present invention relates to a puncture resistant sealable vapour barrier sterilisation bag capable of withstanding a steam sterilisation process whilst providing an effective microbiological barrier having a first sealable opening suitable for receiving items to be sterilised and a second sealable opening adapted to couple to a sterilisation conduit. A third sealable opening may be provided in the bag to facilitate circulation within the bag via the second and third openings when the first opening is sealed. The bag forms the means for sterilising an article(s) solely within the plastic bag in conjunction with a sterilisation services supply device. The bag is preferably formed of plastics. Preferably a multilayer construction including a puncture resistant outer layer and a heat-sealable inner layer. The bag may include a covert marking technology and/or a readable unique identification code such as a tamper-resistant label applied to the bag to facilitate uniformity and traceability.

12 Claims, 5 Drawing Sheets

(58) Field of Classification Search
USPC .................................................. 383/41, 102
See application file for complete search history.

(56) References Cited

U.S. PATENT DOCUMENTS

| | | | | |
|---|---|---|---|---|
| 4,654,240 | A * | 3/1987 | Johnston | 206/524.6 |
| 4,991,633 | A * | 2/1991 | Wong | 141/5 |
| 5,165,539 | A * | 11/1992 | Weber | A61L 2/26 |
| | | | | 206/363 |
| 5,356,006 | A * | 10/1994 | Alpern et al. | 206/363 |
| 6,312,645 | B1 | 11/2001 | Lin et al. | |
| 6,503,183 | B1 * | 1/2003 | Bennish et al. | 493/334 |
| 6,749,808 | B1 * | 6/2004 | Huynen et al. | 422/28 |
| 6,986,605 | B1 * | 1/2006 | Allen et al. | 383/101 |
| 2003/0072701 | A1 * | 4/2003 | Lin et al. | 422/292 |
| 2004/0081601 | A1 | 4/2004 | Morrissey et al. | |
| 2004/0197248 | A1 | 10/2004 | Hasegawa et al. | |

FOREIGN PATENT DOCUMENTS

| | | |
|---|---|---|
| WO | WO-2004071308 | 8/2004 |
| WO | WO-2007055595 | 5/2007 |

OTHER PUBLICATIONS

Mercer Techoloqies Limited, Application No. 10741461.7-2113/ 2396228 PCT/NZ2010000021 Supplemental European Search Report dated Jan. 3, 2013.

\* cited by examiner

STERILISATION BAG

CROSS-REFERENCE TO RELATED APPLICATION

The present patent application is a national phase application of International Application No. PCT/NZ2010/000021, filed Feb. 12, 2010.

FIELD OF THE INVENTION

The present invention relates to an impervious sealable packaging (plastic bag) forming the means for sterilising an article(s) solely within the plastic bag. The packaging, in a preferred form, having the construction of a non-porous, impenetrable receptacle fed through an orifice clamped hermetically about a sterilisation fluid conduit during the sterilisation process of a load (articles) and the package sealed under partial vacuum at the conclusion of a successful sterilisation cycle.

BACKGROUND OF THE INVENTION

The applicants prior application published as WO2007/055595 discloses a sterilisation method and apparatus in which items to be sterilised may be sterilised within a plastic bag whilst the exterior of the sterilisation bag is maintained at atmospheric pressure. The disclosure of this application is hereby incorporated by reference.

In a healthcare facility it is necessary that all equipment and materials used for treating patients are safe for use; the chance of spreading infection should be minimal. As is well known, articles used in the operating room, such as surgical instruments, must be sterilised before and after each use.

In current practice at the end of a correct sterilisation process, articles inside the steriliser chamber are sterile. The air in the room where the steriliser is installed contains dust particles, which may carry microorganisms; therefore the potential exists when taking out the load from the steriliser that it may be contaminated again.

Additionally sterile articles are usually stored for quite some time before use and moreover they are transported through the healthcare facility to the place they are to be used. It is thus obvious that when not protected the goods may be re-contaminated by the time they are used.

Articles therefore must be placed in a packaging to prevent recontamination after sterilisation and at the same time the packaging should be suitable to allow sterilisation of the articles it contains within a steriliser chamber. Packaging is essential for maintaining sterility; moreover the packaging must protect its load against damage during handling and transport.

Current practices of packaging depending on the use, storage and transportation, dictates that a sterile article should be packaged in one or more packaging layers. The inner primary packaging prevents recontamination of the articles after sterilisation and should provide an effective microbial barrier whilst it must allow the passage of air and the sterilant. The secondary layer is applied to facilitate proper storage and transport protection of the articles whilst it must allow the passage of air and the sterilant and in addition the combination of the packaging layers must allow the passage of air and the sterilant. The 'barrier' to microbiologic ingress is thus defined as a torturous path.

The combination of the packaging layers therefore must function as a sterile barrier system enabling medical articles to be sterilised, maintain sterility and ensure the articles sterility until the time of use or the packaging expiry date. The ISO definition of a sterile barrier system is "a minimum package that prevents ingress of micro-organisms and allows aseptic presentation of the product at the point of use".

Due to current sterilisation practices the sterile barrier system is required to be "breathable" and sterile, packaging is the single biggest challenge to successful sterilisation. Due to the requirement of the packaging to act as a barrier once sterile—it is inherently difficult to extract air, insert steam and subsequently extract the resultant condensate to leave the load dry, through this barrier system. Advances in non-woven wraps with their more effective barrier construction have contributed to compounding this problem.

Fundamental to air extraction is the rate at which the air to be removed from the pack can physically pass through the barrier. No allowance for load sizing or service (water pressure/steam supply) variance or time-based extraction is implemented. A common problem with today's sterilisers is the vacuum system is too efficient and the vacuum stages happen faster than the air can get out through the barrier (A common symptom of this is packs 'blowing up' under vacuum). Conversely the pressure stages that are supposed to force steam into the packs are also too efficient and the steam simply cannot penetrate effectively in the time allowed.

This very typical problem encountered with breathable sterile barrier systems is made even worse by lightly loaded cycles or mixed loads where some porous packs are in with non-porous instrument cases etc. and results in inadequate air removal, steam penetration failure and non-sterile packs within the loads.

Traditionally packaging materials were reusable but due to their inadequate microbial barrier properties most of these traditional materials do not meet the requirements for primary sterile packaging anymore. Presently non-wovens, laminated film pouches, paper bags and containers are used as primary packaging materials. These include muslin wraps, various paper wraps and non-woven wraps, or alternatively laminated film pouches or sterilisation containers. The wraps are typically secured by autoclavable tape which may become detached during processing or in the handling of a package leading to rejection of the package. An important feature of fabric is its "breathability" or the ability of the fabric construction to allow the passage of air and water vapour (i.e. steam). Current practices where breathable packaging is required to allow the passage of the sterilant (water vapour/steam) in and out of the package during the sterilisation process places huge demands on the breathable packaging at the conclusion of the sterilisation process to then act as a viral and Liquid barrier to ensure impervious protection of the terminally sterile load. The sterilised package should be constructed so that it may be easily opened without the packaging contaminating the contents.

The minimum requirement of any packaging configuration is that it will maintain sterility of the package load until aseptic presentation at the point of use.

Due to the many variables sterilisation services practitioners are faced with everyday new standards are evolving and the International Organisation for Standardisation (ISO) is working globally to coordinate standards.

The most recently published standard titled "Packaging for terminally sterilised medical devices" has two parts namely; Part 1: Requirements for materials, sterile barrier systems and packaging systems, and Part 2: Validation requirements for forming, sealing and assembly processes.

The emphasis is clearly on patient safety regardless of where or how the product is sterilised.

The dichotomy of the sterile barrier system persists in current practices and the challenge for the packaging suppliers and users is that the sterile barrier system must be porous or breathable to facilitate air removal and sterilant penetration/removal during the sterilisation process within the steriliser and then crucially at the completion of a successful sterilisation process, provide impervious protection as a viral and liquid barrier until aseptic release at point of use.

Not withstanding the substantial research and investment in breathable sterile barrier systems the necessity of the barrier material to be breathable during the sterilisation process/cycle in the steriliser chamber and then conversely an impervious barrier system after sterilisation is extremely unlikely. This conflicting demand of the breathable barrier system has no perfect solution and remains one of those dilemmas hard to solve.

The applicant's prior application published as WO2007/055595 discloses a plastic sterilisation bag having a single opening for receiving items to be sterilised and for conveying sterilant. Whilst simple and effective the items are not sealed within the bag until after sterilisation and it is more difficult to seal a large opening than a small opening.

It is an object of the invention to provide an improved sterilisation bag or to at least provide the public with a useful choice.

SUMMARY OF THE INVENTION

There is thus provided a puncture resistant sealable vapour barrier sterilisation bag capable of withstanding a steam sterilisation process whilst providing an effective microbiological barrier having a first sealable opening suitable for receiving items to be sterilised and a second sealable opening adapted to couple to a sterilisation conduit.

The first sealable opening is preferably formed by adjacent walls of the bag being substantially unjoined along one edge of the bag. The second sealable opening is preferably in the form of a neck that is relatively narrow with respect to the width of the bag. A third sealable opening may also be formed communicating with an internal channel that extends sufficiently into the bag to facilitate circulation within the bag via the second and third openings when the first opening is sealed.

The bag is preferably formed of plastics. It may be formed from a sheet of multilayer construction. The bag may be formed of a sheet that is folded and sealed along part of its adjacent edges. The bag is preferably capable of withstanding internal process temperatures up to 138 degrees Celsius and external process temperatures of up to 180 degrees Celsius. The bag preferably has a puncture resistant outer layer and a heat-sealable inner layer. The bag material construction may be translucent to facilitate visual verification of sterilisation process indicators. The contents of the bag may be sealed within the bag at a modified atmosphere allowing visual indication of a breach of the sealed bag integrity.

The bag may include a covert marking technology. The covert marking technology may be a tamper-resistant label applied to the bag. The covert marking technology may be integrated into the bag. The bag may include a readable unique identification code.

BRIEF DESCRIPTION OF THE DRAWINGS

The invention will now be described by way of example with reference to the accompanying drawings in which.

DETAILED DESCRIPTION OF A PREFERRED EMBODIMENT OF THE INVENTION

In response to the challenges encountered by those of skill in the art, from the following description it will be evident that the requirements listed below are desirable:

Enabling Sterilisation

The packaging will allow air that is in the packaging to be evacuated and the sterilant or sterilising agent to be introduced to reach all surfaces of its content (items) via a conduit (snorkel) communicating with an opening (mouth).

Compatible with the Sterilisation Process

The combination of the apparatus and packaging will be able to withstand the conditions that occur during the sterilisation process such as pressure changes, high temperature and humidity.

Ensure Product Integrity and Patient Safety

The sterilisation bag/sterilisation process will not affect the item(s) in any other way, which may affect the quality of the item(s) or which might endanger the patient or process on which the sterile item(s) will be used, subject to the item(s) to be processed being rated for the sterilisation temperature and pressure.

Maintaining Sterility

After taking the sealed and vacuum packed sterile load/item(s) out of the apparatus it/they will remain sterile during handling, transportation and storage until use, whilst package seal integrity is intact.

Packaging Authentication

Authentication of the packaging prior to sterilisation of item(s) is desirable to ensure an authenticated and validated sterilisation bag is derived from tested and approved film to facilitate most appropriate functionality with respect to sterilisation process, sealing integrity, handling, transportation and shelf-life.

Tracking and Traceability

The apparatus and packing may desirably process individual loads/trays with each load/tray incorporating a unique identification code written to a RFID tag (attached to the load) and captured in a database to facilitate data logging of process parameters per individual package and to facilitate full tracking and traceability of individual loads throughout its lifecycle.

Indicator

Transparent sealed packaging to facilitates visual verification of sterilisation process indicators.

Facilitate Aseptic Opening and Presentation

When opening a sealed vacuum packed sterile load/item(s), the packaging will facilitate aseptic opening and presentation.

This implies:

simple opening when removing the sterile load/items from the packaging, package opening will facilitate direct access to the sterile load within the interior of the packaging, the design incorporates an autoclavable perforated tray with lid (preferably of stainless steel mesh construction or similar) that the item(s) are placed in prior to insertion into the packaging (plastic bag). Optionally the tray may be wrapped in a porous fabric/wrap to further enhance aseptic release of the load in theatre or sterile zone.

Visible Indication That Packaged Has Been Opened Or Breached

Subjecting the package to a vacuum state whence sealed after load sterility is achieved enables immediate visible indication of package vacuum loss due to either a fault of seal integrity loss, package integrity breach or package opening under normal controlled aseptic opening of terminally sterile package. In the event that the package has lost its vacuum as a result of a failure the package may be immediately be deemed contaminated and no longer sterile.

Figure 1:
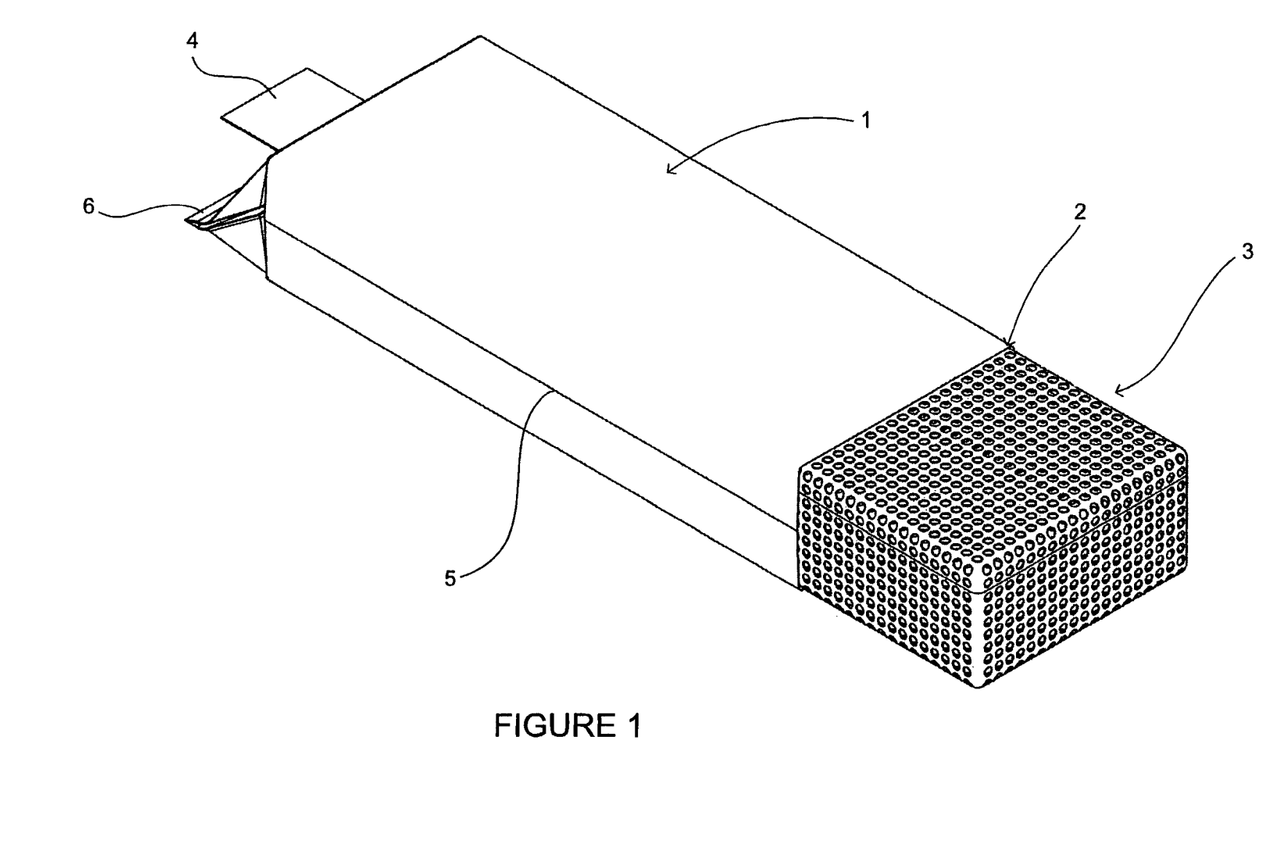
FIG. 1 shows a view of a typical packaging (plastic sterilisation bag) with its loading end open.

Referring to FIG. 1 a sterilisation bag according to one embodiment is shown. The bag 1 has a first opening 2 for receiving items to be sterilised (in this case contained within a perforated cage 3). A second opening is provided at the other end in the form of a tube 4 communicating with the interior of the bag. Tube 4 may be relatively narrow with respect to the width of the bag to ensure the contents may be securely retained when opening 2 is sealed and to facilitate sealing with sterilisation services supply apparatus.

The bag 1 is preferably formed of plastics. The bag 1 may be of multi-layer construction and may be formed of a puncture resistant outer layer and a heat-sealable inner layer. The bag should be capable of withstanding a steam sterilisation process whilst providing an effective microbiological barrier. The bag may advantageously be formed of a transparent material to facilitate visual verification of sterilisation, bag contents and sterilisation process indicators (such as an indicator which changes colour when exposed to required sterilisation parameters). The bag 1 should be capable of withstanding internal process temperatures of up to 138 degrees Celsius and external, process temperatures up to 180 degrees Celsius.

The bag may be formed from a sheet of such material by cutting the required outline from a sheet of material, folding the bag and heat sealing together edges 5 and 6 and the edges of the opposite sides of tube 4. Alternatively the bag may be formed from a tube with one end cut to define the sides of tube 4 and the edges heat sealed (apart from the tube opening).

Figure 3:
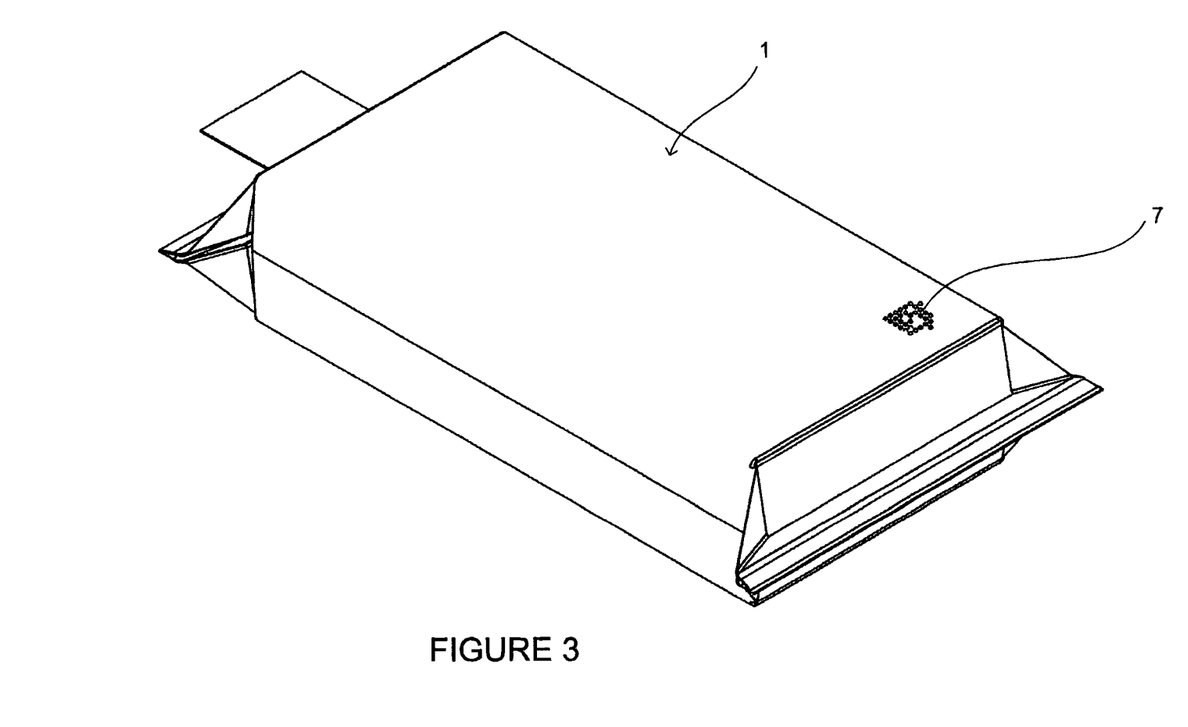
FIG. 3 shows the packaging of FIG. 1 containing the tray shown in FIG. 2 with the load end sealed and ready to be sterilised.

The bag may include an authentication feature 7 as shown in FIG. 3. In one embodiment this may be a tamper resistant label including a code, such as a bar code. Preferably each sterilisation bag is assigned a unique identification code so that each bag may be uniquely identified and tracked. Alternatively the identification feature may utilise a covert marking technology integrated into the bag, such as a non-visible marking, a nano-technology feature etc. The identification feature may identify a bag type where different bag types are used for different applications or bag validity or it may contain a code uniquely identifying the bag.

Figure 2:
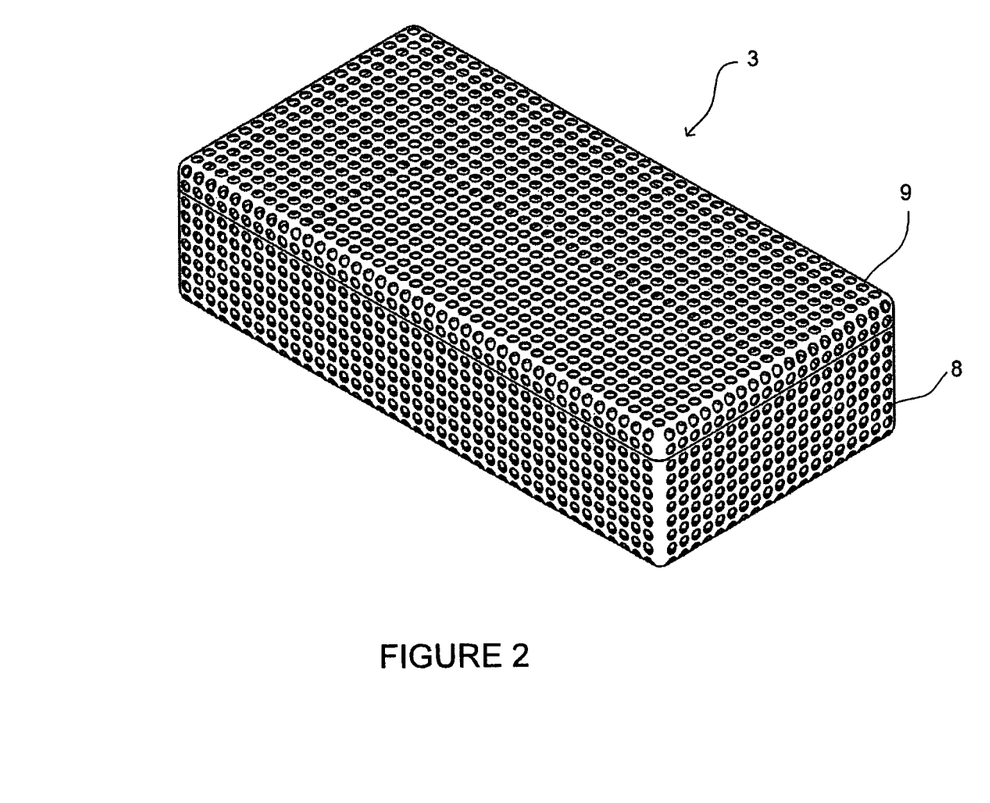
FIG. 2 shows a perforated tray for containing items to be sterilised.

In use items to be sterilised may be placed within cage 3 (FIG. 2) by removing lid 9, placing items to be sterilised in base 8 and replacing lid 9. The cage 3 containing the items to be sterilised may then be placed within bag 1 as shown in FIG. 1. Once the cage 3 is fully inserted opening 2 may be sealed. Opening 2 is preferably sealed by heat sealing the edges of bag 1 adjacent opening 2. However, other sealing methods, such as using adhesives, could be employed. The sealed bag shown in FIG. 3 now securely contains the contents and has a unique identifier in the form of identification feature 7 allowing tracking of the package throughout a sterilisation process and for subsequent inventory management.

Figure 4:
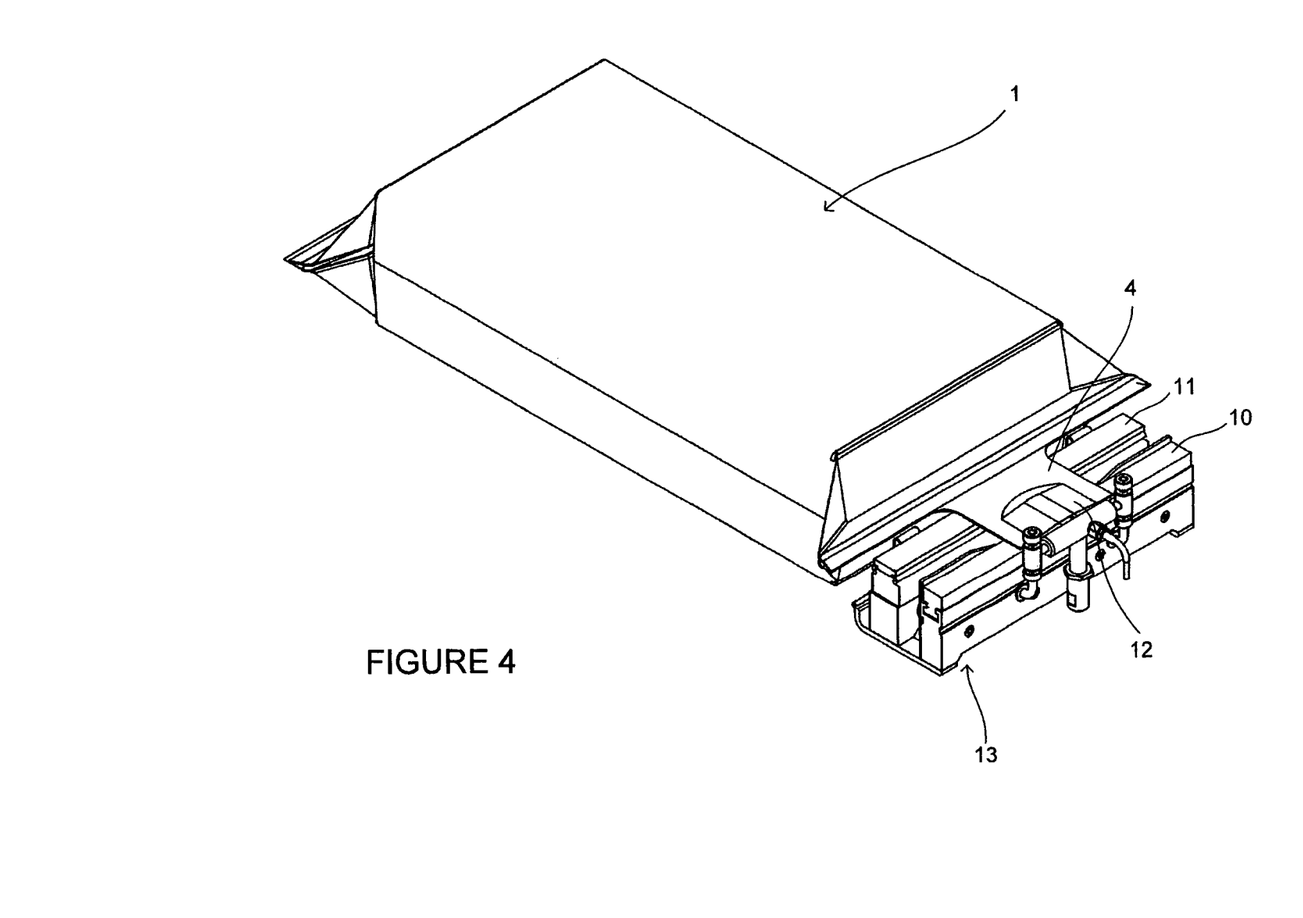
FIG. 4 shows an opening of the packaging encapsulating a snorkel supplying sterilisation services.

Referring now to FIG. 4 a bag 1 is shown connected to the supply connection 13 of a sterilisation services apparatus. It will be seen that a conduit 12 is inserted within the opening of tube 4. Conduit 4 tapers towards its edges to facilitate sealing. In use a resilient bar (similar to bar 10) is pressed against bar 10 to provide a clamping pressure to seal tube 4 against conduit 12. The bag may then be evacuated via conduit 12, sterilant (typically steam) may then be supplied to sterilise the contents, the contents may then be dried and then the bag evacuated. At the completion of the sterilisation process, and whilst the bag is at least partially evacuated, tube 4 may be sealed. In a preferred embodiment a heat sealing bar may be forced against heat-sealing bar 11 to heat seal tube 4. Thus a sealed bag containing sterilised items protected from external conditions is produced and can be safely moved and stored. When sterilised items are required bag 1 may be removed and the contents removed from cage 3.

Figure 5:
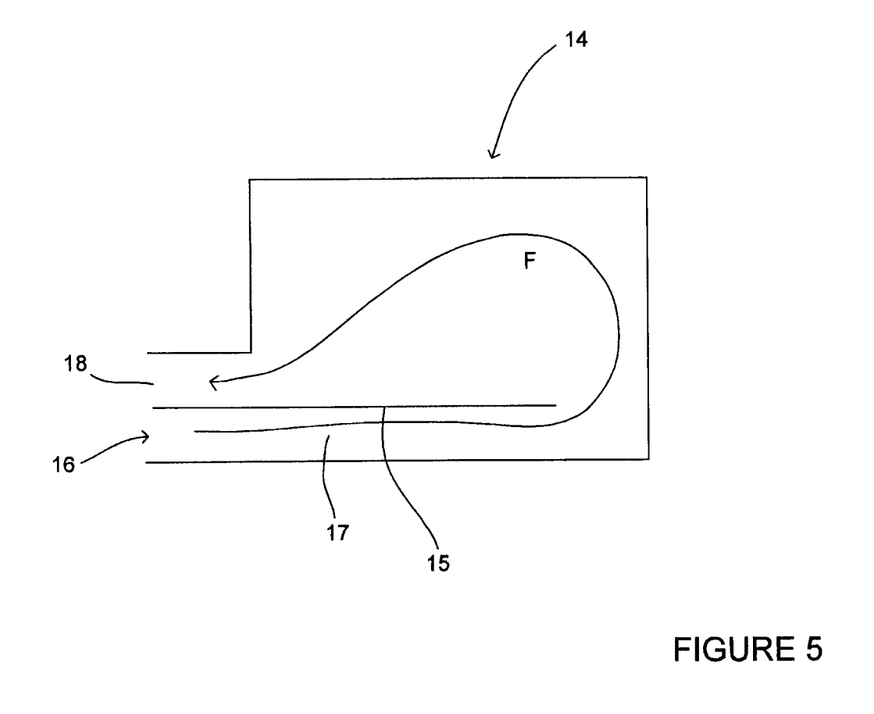
FIG. 5 shows a bag according to an alternate embodiment having an additional opening communicating via a channel to the interior of the bag.

According to an alternate embodiment shown conceptually in FIG. 5 the bag shown in FIG. 1 may be modified to include a further opening and a channel for supplying fluid to the interior of the bag. Bag 14 is generally as shown in FIG. 1 except that the sides of the bag are heat-sealed together along seal line 15 to define a further opening 16 and a channel 17. This construction facilitates circulation of fluid within the bag so that fluid may be supplied via opening 16, along channel 17, within bag 14 and out of opening 18 as indicated by arrow F. It will be appreciated that this arrangement requires two conduits to be engaged with respective openings 16 and 18.

The invention according to one embodiment is envisaged to accommodate a load containing one tray/cage of half a sterilising unit [½ StU=30 cm×15 cm×60 cm (W×H×L)] per package, thereby facilitating and promoting standardisation of individual load dynamics. This is by way of example and the invention is not limited to this standard size.

The sterilisation bag will need to be made to required specifications, specific to each application. The package (and film) will be impervious and non-porous to facilitate the parameters of steam sterilisation and be able to hold a vacuum for a prolonged period under sealed conditions.

Means may be incorporated in sterilisation services supply apparatus used with the bag to enable the apparatus to either accept or reject a sterilisation bag through a process of authentication and/or unique identification marking 7.

The sterilisation bag according to the present invention therefore preferably comprises a multilayer packaging film that combines desired properties such as viral barrier properties, strength, heat sealability and is suitable for being made into a bag. Preferably, the multilayer packaging film is provided with at least one heat sealable layer and a sterile barrier layer (preventing ingress of micro-organisms and allowing aseptic presentation).

When the multilayer packaging film is made into a bag, it is preferred that the inner layer of the bag is the heat sealable layer. The sealing operation, is usually performed inside to inside, therefore the first transverse seal is made to shape the film into a tube and the top of the tube is sealed to form an open mouth and this is the production fabricated package.

The large opening 2 of a sterilisation bag 1 may be sealed in a sterile services facility (department) after the load/tray containing the articles to be sterilised have been placed in the package, preferably on a packaging table (station) and sealed in an approved sealing machine.

The mouth of the tube 4 is sealed under controlled conditions within a sterilisation services supply apparatus after a successful completion of a sterilisation process, effectively sealing the terminally sterile load within an impervious sterile barrier system under a partial vacuum. The packaging shall then remain sealed until aseptically opened at point of use or alternative until the expiry date. The shelf life of the sealed impervious package is expected to substantially exceed existing breathable sterile barrier systems.

Besides the heat sealable layer and barrier layer, the multilayer film may comprise further layers, e.g. layers that provide higher toughness, clarity, stiffness, strength and the like. In the preferred form the film shall be a triplex (three laminate) construction. The invention in the preferred form is envisaged that the package shall be converted from a triplex laminate film made up of PET/Biax Nylon/CPP or similar as will be appreciated by those skilled in the art.

The preferred film shall have a clear outer Natural PET (polyethylene terephthalate) laminate which provides high tensile strength and heat resistance, the second Biaxally Oriented Nylon laminate provides excellent barrier properties, and good pinhole/puncture resistance and the inner laminate is a Special Retort CPP (Cast Polypropylene) providing heat sealability and high seal strength.

Part 1 of the EN ISO 11607 specifies the general requirements for all sterile barrier systems. Part 2 of EN ISO 11607 describes the validation requirements for forming, sealing and assembly processes of sterile barrier systems.

Three levels of sterilisation products are being defined:

1. Sterile Barrier System: minimum package that prevents ingress of microorganisms and allows aseptic presentation of the product at the point of use
2. Protective Packaging: configuration of materials designed to prevent damage to the sterile barrier system and its contents from the time of assembly until the point of use
3. Packaging system: combination of the sterile barrier system and protective packaging The invention according to one embodiment shall provide an impervious sterile barrier system offering complete viral barrier protection against ingress of microorganisms whilst the packaging seal integrity is maintained. In a further embodiment the packaging containing the terminally sterile load (DIN 58952/ISO instrument tray/basket size) under partial vacuum is planned to be of capacities to DIN or ISO sizing as per sterile units typically ½ StU to comply with the ISO modular system for Slide in-sterile goods baskets.

The combination of an impervious sterile barrier system and protective packaging system in the form of the carrier goods basket offers a complete packaging system. A further embodiment of the invention is the overt/covert authentication system to validate the packaging and film authenticity to facilitate sterile barrier uniformity and repeatability and coupled with the overt serialisation—Unique Identification mark (UIM) system, full quality assurance will be possible for the packaging system.

In one form of the invention the authentication incorporated on every package may be based on a covert marking technology (such as a nano-technology technique) facilitating quality assured supply chain logistics of the packaging and sterilisation process. The authentication of the packaging and film therefore ensures the use of only the validated and internationally regulatory approved film laminates as sterile barrier system thereby endorsing the ISO 11607 standard.

The invention provides a solution utilising a non-porous (non-breathable) sterile barrier system during an in-bag sterilisation process which due to the impervious qualities provides a sterile barrier system after sterilisation. This replaces the necessity for a breathable sterile barrier system and the large and inefficient steriliser chambers of the prior art.

The sterile load remains securely within the impermeable package offering a sterile barrier system with full viral and liquid barrier protection. In principle the probability of recontamination is completely eliminated whilst the package seal integrity is maintained.

It is anticipated that the method of sterilisation solely within the package will provide substantial efficiencies in the sterilisation process model. The process will remove air from directly inside the packaging within seconds/minutes whilst pre-heating the load, sterilisation parameters of pressure and time will adhere to international recognised standards (typically 3.5-5 minutes @ 134° C. (degrees Celsius) of steam penetration to facilitate sterilisation) followed by the drying phase by means of removing the majority of the steam/condensate through pulling a vacuum in the package whilst the package is located on a heating plate, drying will be facilitated within minutes.

It is envisaged that most sterilisation cycle time(s) may be reduced by more than 50%, subject to the load mass. The packaging containing the sterilised load (items) will be vacuum sealed at the end of the sterilisation cycle and it is believed that the invention will result in less likelihood of wet load problems due to direct heat transfer of heat from a heating plate during the drying phase.

Furthermore due to non-use of traditional wrapping fabrics (which inhibits the vapour removal due to the inherent tortuous path), vacuum drying efficiency is greatly enhanced. The package also has greater integrity reducing rejection due to mechanical packaging failure during processing and handling. The packaging material also allows easy opening due to the clean tearing of the material the risk of contamination from the packaging is low.

The shelf-life of a sterile load(s) shall be monitor friendly (visual identification that vacuum has been maintained by the bag adhering to the cage), facilitate quality assurance and offer longer expiry dates.

The invention as described herein is open to modification as will be appreciated by those skilled in the art. For example, rather than perform as a sterilisation package the packaging could be used as a retort or food cooking package but not limited to only these applications.

Other modifications and improvements to the invention will be apparent to the skilled person and will fall within the scope of the invention as it is intended.

What we claim is:

1. A puncture resistant sealable vapor barrier sterilization bag formed of one or more sheets a non-porous plastic material capable of withstanding a medical grade steam sterilization process having process temperatures up to 138 degrees Celsius whilst providing an effective microbiological barrier, the bag having:
   a first heat sealable opening formed by adjacent walls of the bag being substantially unjoined along one edge of the bag and being suitable for receiving items to be sterilized;
   a second heat sealable opening in the form of a neck that is relatively narrow with respect to the width of the bag, the neck adapted to couple to a sterilization conduit; and
   a third sealable opening formed communicating with an internal channel, wherein the internal channel is formed by heat sealing a line between adjacent walls of the bag and extends sufficiently into the bag to facilitate circulation within the bag via the second and third openings when the first opening is sealed.

2. A bag as claimed in claim 1 wherein the bag is formed of a sheet that is folded and sealed along part of its adjacent edges.

3. A bag as claimed in claim 2 wherein the bag has a puncture resistant outer layer and a heat-sealable inner layer.

4. A bag as claimed in claim 1 wherein the bag is formed of a sheet of multilayer construction.

5. A bag as claimed in claim 4 wherein the bag is capable of withstanding internal process temperatures up to 138 degrees Celsius and external process temperatures of up to 180 degrees Celsius.

6. A bag as claimed in claim 1 wherein the bag includes a covert marking technology.

7. A bag as claimed in claim 6 wherein the covert marking technology is a tamper-resistant label applied to the bag.

8. A bag as claimed in claim 6 wherein the covert marking technology is integrated into the bag.

9. A bag as claimed in claim 6 wherein the bag includes a readable unique identification code.

10. A bag as claimed in claim 1 wherein the bag material construction is translucent to facilitate visual verification of sterilization process indicators.

11. A bag as claimed in claim 1 wherein the contents of the bag are sealed within the bag at a modified atmosphere providing visual indication of any breach of the sealed bag integrity.

12. A bag as claimed in claim 1 wherein the bag contains a rigid cage to contain items to be sterilized.

* * * * *